(12) United States Patent
Morgenstern

(10) Patent No.: US 6,545,193 B1
(45) Date of Patent: Apr. 8, 2003

(54) ELASTIC BANDAGE WITH CRISS-CROSSED HOOK AND LOOP FASTENERS

(76) Inventor: Michael Morgenstern, 147-27 75 Ave., Flushing, NY (US) 11367

( * ) Notice: Subject to any disclaimer, the term of this patent is extended or adjusted under 35 U.S.C. 154(b) by 0 days.

(21) Appl. No.: 09/718,123

(22) Filed: Nov. 17, 2000

Related U.S. Application Data (63) Continuation-in-part of application No. 09/251,210, filed on Feb. 16, 1999, now abandoned.

(51) Int. Cl.[7] ................................................ A61F 13/00
(52) U.S. Cl. .......................... 602/41; 602/75; 128/876; 128/DIG. 15
(58) Field of Search ............................ 602/1, 5, 60–66, 602/74–75, 41; 128/876–877, DIG. 15; 428/99, 100

(56) References Cited

U.S. PATENT DOCUMENTS

| | | | |
|---|---|---|---|
| 3,256,882 A | | 6/1966 | Huber |
| 3,338,028 A | | 8/1967 | Freeman |
| 3,442,270 A | * | 5/1969 | Steinman ............. 128/DIG. 15 |
| 3,504,672 A | | 4/1970 | Moon |
| 3,529,601 A | * | 9/1970 | Kirkland ........................ 601/1 |
| 3,613,679 A | * | 10/1971 | Bijou ........................... 602/75 |
| 3,880,161 A | | 4/1975 | Fosset |
| 4,022,197 A | * | 5/1977 | Castiglia ..................... 128/96.1 |
| 4,085,746 A | * | 4/1978 | Castiglia .............. 128/DIG. 15 |
| 4,527,566 A | | 7/1985 | Abare |
| 4,846,164 A | * | 7/1989 | Martz ........................... 428/90 |
| 4,926,848 A | | 5/1990 | Shimkus et al. |
| 4,991,234 A | | 2/1991 | Greenberg |
| 5,069,457 A | * | 12/1991 | Korenowski ......... 128/DIG. 15 |
| 5,107,827 A | | 4/1992 | Boyd |
| 5,137,508 A | * | 8/1992 | Engman ..................... 119/850 |
| 5,938,631 A | | 8/1999 | Colman |
| 6,080,347 A | * | 6/2000 | Goulait ................. 156/244.22 |

* cited by examiner

*Primary Examiner*—Michael A. Brown
*Assistant Examiner*—Quang D. Thanh

(57) ABSTRACT

An elongated elastic bandage includes a plurality of hook fastener strips on a first side and a plurality of loop fastener strips on a second side. The hook fastener strips are generally aligned with the longer dimension of the elastic bandage while the loop fastener strips extend across the width of the bandage. In use, the hook and loop fastener strips form a criss-cross configuration when the elastic bandage encircles a portion of a users body.

3 Claims, 14 Drawing Sheets

ELASTIC BANDAGE WITH CRISS-CROSSED HOOK AND LOOP FASTENERS

This is a continuation-in-part of application Ser. No. 09/251,210, filed on Feb. 16, 1999, now abandoned.

BACKGROUND OF THE INVENTION

1. Field of the Invention

The present invention relates generally to the field of bandages and more particularly to elastic bandages with criss-crossed hook and loop fasteners for encircling and supporting a portion of the user's body.

2. Prior Art

Elastic bandage wraps can be used to provide support, compression, and/or immobilization for joints and limbs. Application of these bandages typically employ figure eight pattern type wrapping and the bandages are commonly wrapped in a continuous manner. In wrapping a user, it is common practice to initially have the bandage rolled neatly and to wrap the bandage around a portion of the body as the bandage is being unrolled. In order to apply the bandages in this fashion, the bandages are usually of a considerable length such as four feet or greater. Elasticized bandages and more specifically elastic bandages which are elastic in the longitudinal direction present significant advantages over their non-elastic counterparts. These advantages include an increased ability to accommodate the curvature of body parts, improved ability to stay on without slipping, the ability to apply a relatively even amount of bandage pressure useful for the treatment of ailments and wounds, and the ability to wrap a portion of the body using a significantly shorter and hence a lighter bandage. Elastic bandages are typically retained in a wrapped position by one or more metal clips. The metal clips have relatively sharp projections formed thereon which, when in use, pierce the end of the bandage and also pierce an intermediate portion of the bandage thereby holding the end of the bandage in contact with the intermediate portion of the bandage.

In U.S. Pat. No. 4,748,975, Yashima discloses an elliptical shaped supporter having a longitudinal slit at the center portion to allow for protrusions. The supporter uses a hook and loop closure system. The supporter comprises a plurality of transverse Velcro which is disposed proximate to one end of the supporter and terminates about the midpoint of the supporter. Due to the constraints of being a supporter and not a bandage that can be wrapped, it cannot be used to effectively wrap or support areas of tapering proportions such as the leg, thigh or forearm. Furthermore, because the supporter allows for joints to protrude out its slit no compression is applied directly to the area which projects out of the slit.

In U.S. Pat. No. 3,338,028, Freeman discloses a track bandage for horses which is wrapped in a spiral manner. The bandage includes a hook and loop fastener closure system. The bandage is comprised of a longitudinally disposed loop strip and a longitudinally disposed hook strip. As a result of this, if the bandage were to be brought together angularly the Velcro strips would cross each other over a relatively small area, and the necessary gripping action would be hindered. Furthermore, the bandage's range of adjustability is limited by the length of its longitudinally disposed loop strip in combination with the length of its longitudinally disposed hook strip. In addition the bandage is inelastic in length and suffers from all the disadvantages thereof such as having a long length of nine feet, which makes wrapping an arduous task.

Fossel in U.S. Pat. No. 3,880,161 discloses an elongated elastic bandage with an attached strap bearing hook fastener on one side and loop fastener on the other. Wrapping such a bandage on a user where the fastening element is free to dangle about is a cumbersome process as is the fastening of such a strap attached to a wrapped bandage. This linear arrangement of fastener would also present problems if the fastener were brought together angularly. Additionally, such a fastening element will often leave flapping to occur after attachment, an undesirable result. Furthermore, such a bandage would be unable to be rolled neatly before wrapping because of the variations in the dimensions of the bandage and its attached fastening strip.

An elastic ankle wrap is disclosed in Castigla U.S. Pat. No. 4,085,746. This wrap is initially applied to an ankle by placing a hook fastening tab, on the top of a users foot, engaging that tab with a corresponding loop fastening tab, wrapping a bandage about the ankle and securing the bandage with predetermined corresponding hook and loop fastener patches. The hook fastening tab is attached to the first end of the bandage forming an angle not equal to zero degrees. This arrangement is designed so that the tab can fit onto the foot of a wearer. As a result of this two different wraps are necessary for a right foot and a left foot. The wrap is not suited to be wrapped around any area other than the ankle and foot. Additionally, although the wrap could be used for support it cannot be used for immobilization of the ankle joint.

The prior art also includes the device shown in Greenberg U.S. Pat. No. 4,991,234. This device includes patches of hook and loop fasteners which extend across the entire width of an elastic band. The device is designed to form a tubular support for the wrist or waist by linearly wrapping one area and reinforcing the initial wrap. The device is directed toward providing an anchor point by allowing an intermediate hook segment to engage a starting end loop segment after an initial wrap of the band and providing a terminating hook segment which engages a loop segment to secure the end of the band. The hook and loop segments are in the form of patches which extend across the width of the band, resulting in an unwanted degree of stiffness and lack of adjustability. The Greenberg device is directed toward providing a cylindrical tubular configuration for wrapping the wrist or the waist of a user. It cannot be used to wrap in a figure eight pattern of wrapping and cannot be used effectively in other applications such as wrapping the leg, thigh or forearm of a user because of the tapering proportions of these body parts.

OBJECTS AND SUMMARY OF THE INVENTION

It is therefore an object of the present invention to provide an elastic bandage, which contains elasticity in the longitudinal direction, which incorporates hook and loop fasteners which may form a criss-crossed configuration when the elastic bandage is applied to the user's body.

It is another object of the present invention to provide an elastic bandage which can effectively fasten at an angular arrangement.

Still another object of the present invention to provide an elastic bandage which will provide a large surface area of attachment for hook portions of the bandage and thereby allow to the bandage to be engaged without being uncomfortable to the wearer or allowing hook portions to become engaged with clothing or the like.

Another object of the present bandage is to provide an elongated wrap which may be used to provide support, compression, and/or immobilization of joints or limbs.

Another object of the present invention is to provide an elastic bandage which can be applied in a spiral, figure eight, and/or continuous manner to support a portion of a user's body and which can be secured in an effective manner.

A further object of the present invention is to conveniently allow for a bandage to fit on a large range of proportions with relatively few fastening attachments.

Yet another object of the present invention is to provide an elastic bandage with criss-crossed hook and loop fasteners which can be manufactured at a relatively low cost.

Another object of the present invention is to teach a method for rolling such a bandage which would permit for easy application of the bandage.

The foregoing and other objects and advantages of the present invention will appear more clearly hereinafter.

In accordance with the present invention there is provided an elastic bandage with cross-crossed hook and loop fasteners which includes a generally rectangular elastic bandage. The present invention's elements allow for a great range of adjustability without that adjustability impairing the elasticity of the bandage. By adding longitudinally disposed narrow hook strips on one side and one end of the generally rectangular bandage, a plurality of narrow loop portions on a second side of the bandage and generally at the same end of the bandage, and a bandage which includes longitudinal elasticity, an unexpectedly large amount of adjustability is created. The narrow loop portions may extend across the majority of the width of the elastic bandage.

It will be appreciated that the present invention contemplates having longitudinally disposed loop strips on one surface and one end of the bandage and a plurality of transversely disposed hook strips generally at that same end on a second surface of the bandage. However, the preferred embodiment of the present invention includes, as mentioned above, longitudinally disposed hook strips and a plurality of transversely disposed loop strips and the following specifications and drawings will reflect the embodiment of the preferred method. The use of this embodiment however should not be construed as limiting the scope of the present invention.

In use, when the elastic bandage is applied to a portion of a user's body, the hook and loop fastener portions cross at an angle and thereby secure the end of the elastic bandage.

BRIEF DESCRIPTION OF THE DRAWINGS

Other important objects and advantages of the present invention will be apparent from the following detailed description taken in connection with the accompanying drawings wherein like numerals refer to like parts and in which.

DETAILED DESCRIPTION OF THE INVENTION

Referring to the drawings, wherein like reference numbers designate like or corresponding parts throughout, there is shown in FIGS. 1–27 an elastic bandage with crisscrossed hook and loop fasteners 10, made in accordance with the present invention.

Figure 1:
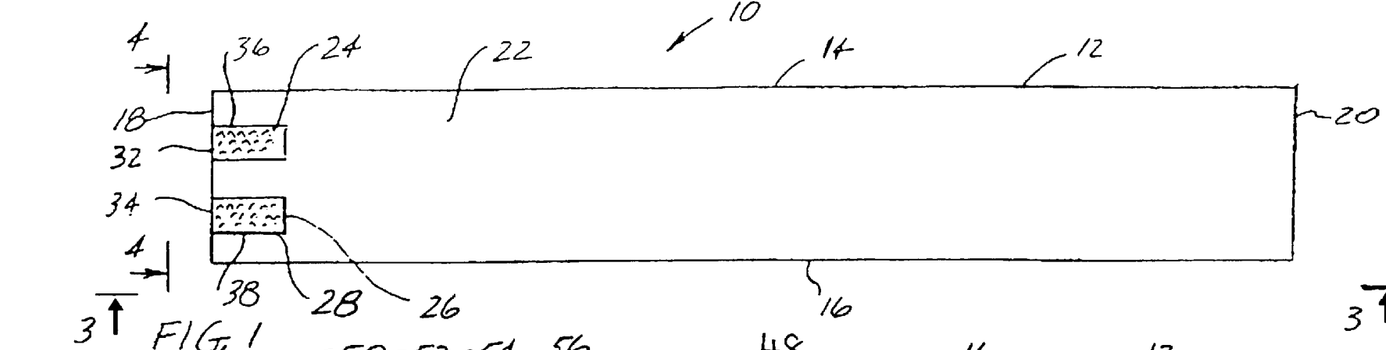
FIG. 1 is a top plan view of an elastic bandage with cross-crossed hook and loop fasteners made in accordance with the present invention.

The elastic bandage 12 is generally rectangular and is defined by relatively loner edges 14, 16 and relatively shorter edges 18, 20. The bandage 12 is flexible and is made of woven or knitted fabric which incorporates elastic yarn. The elastic bandage 12 is preferably elastic in any direction to permit multi-directional elongation.

Figure 11:
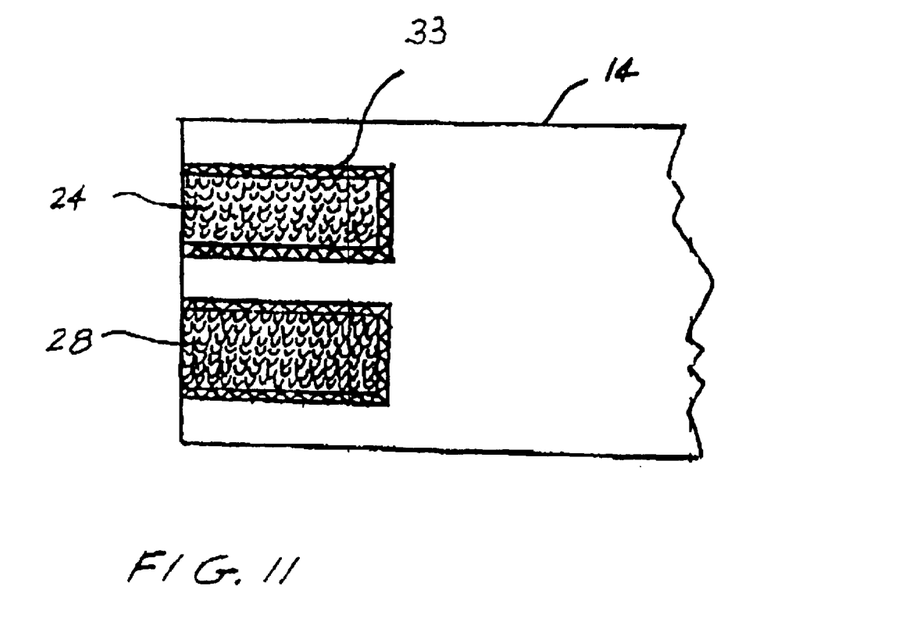
FIG. 11 is a fragmentary top view of the elastic bandage of FIG. 1, drawn to an enlarged scale.

FIG. 1 shows the first side 22 of the elastic bandage 12. A pair of rectangular portions of hook portions 24, 26 which are part of a hook and loop fastener 28 are attached to the first side 22 of the elastic bandage 12 in a conventional manner such as by an adhesive layer 30 or, alternatively, as is best shown in FIG. 11, by stitching 33.

As is shown in FIG. 1, the edges 32, 34 of the hook portions 24, 26 are generally in line with the edge 18 of the elastic bandage 12 and the edges 36, 38 of the hook portions 24, 26 are generally in line with the edges 14, 16 of the elastic bandage 12.

Figure 2:
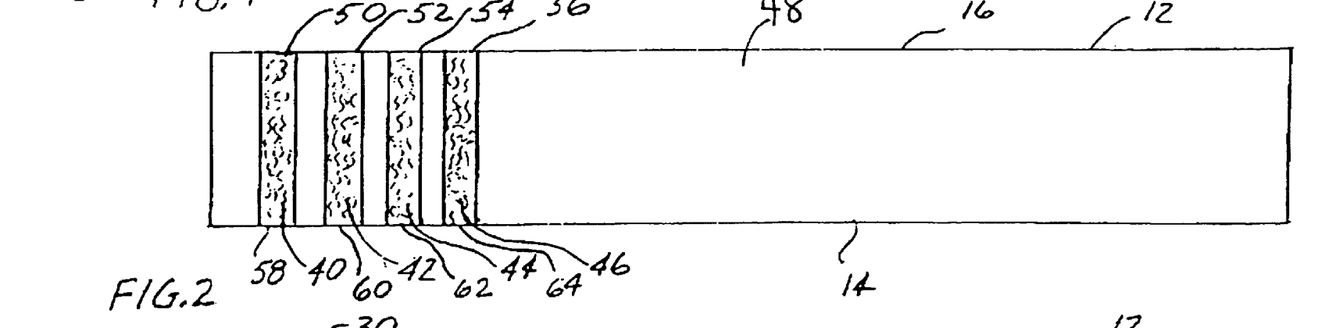
FIG. 2 is a bottom plan view of the elastic bandage of FIG. 1.

As is shown in FIG. 2, a plurality of loop portions 40, 42, 44, 46 are attached to the second side 48 of the elastic bandage 12. The loop portions 40, 42, 44, 46 are configured as relatively narrow rectangular portions which extend across the width of the elastic bandage 12.

The ends 50, 52, 54, 56 of the loop portions 40, 42, 44, 46 are generally in line with the edge 16 of the elastic bandage 12 and the ends 58, 60, 62, 64 are generally in line with the edge 14 of the elastic bandage 12.

Figure 3:
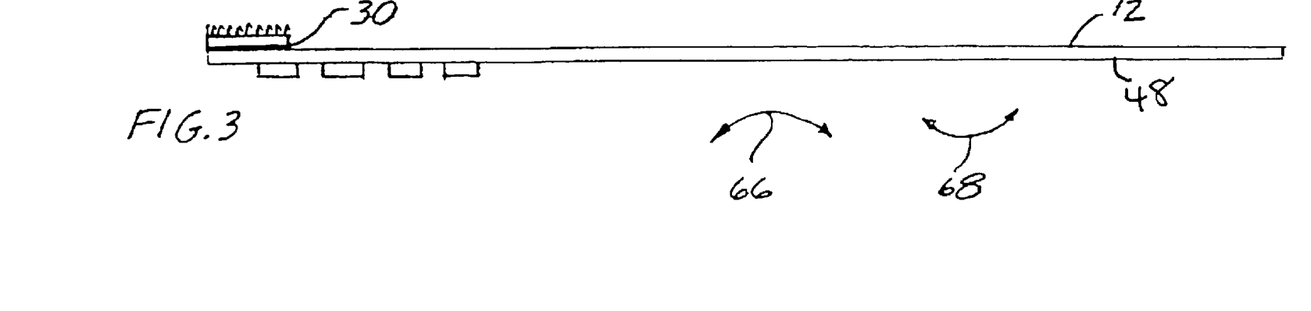
FIG. 3 is a side view of the elastic bandage taken along line 3—3 of FIG. 1.
Figure 4:
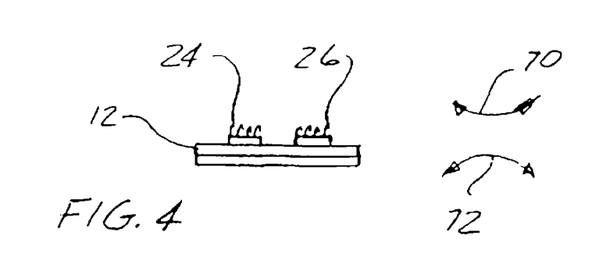
FIG. 4 is an end view of the elastic bandage taken along line 4—4 of FIG. 1.

During use, the individual hook and loop fastener portions 24, 26, 40, 42, 44, 46 allow the elastic bandage 12 to bend freely in the directions shown by the arrows 66, 68, 70, 72 in FIGS. 3 and 4, thereby enabling the use of the elastic band to be applied to various portions of the body including legs, arnis and thighs which have a convexly curved shape. The individual hook and loop fastener portions 24, 26, 40, 42, 44, 46 allow the elastic bandage 12 to be applied in a spiral or a tubular manner.

Figure 12:
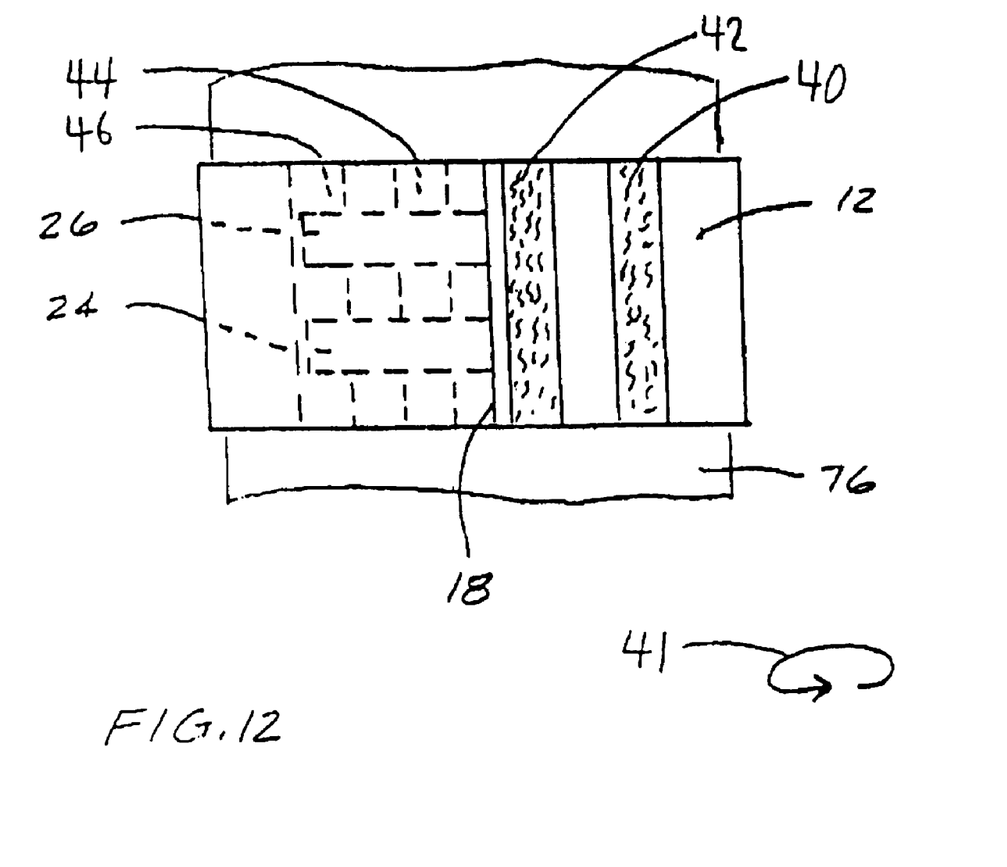
FIG. 12 is a fragmentary view of the elastic band of FIG. 1, with the elastic band shown, in use, applied to a body part.
Figure 13:
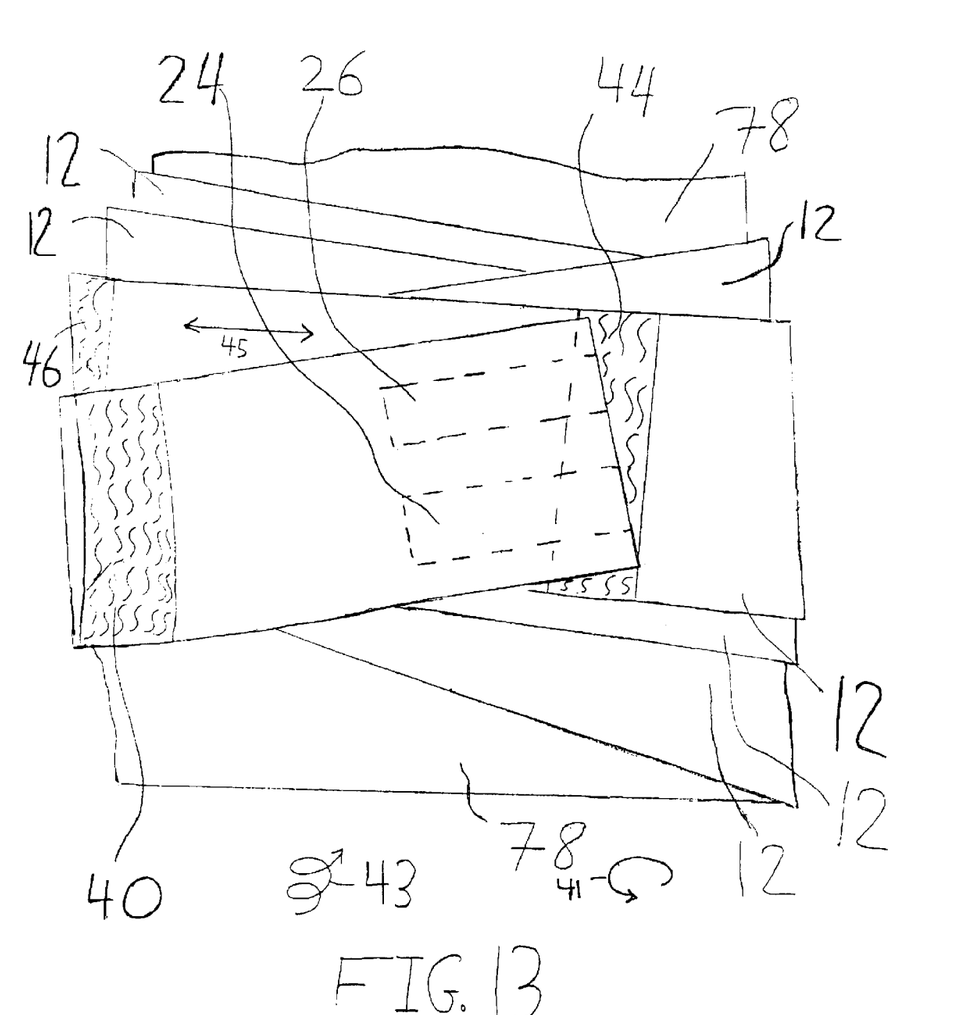
FIG. 13 is a fragmentary view, similar to FIG. 12, with the elastic bandage shown, in use, applied to a tapered body part; to FIG. 14 is a side view of the bandage according present invention prior to the process of wrapping.

When the elastic bandage 12 is applied to a portion of the user's body 76 in a spiral manner, the hook portions 24, 26 cross-cross the loop portions 44 and 46 as shown in FIG. 12 and loop portions 40 and 42 could be utilized to secure the bandage in a tighter fashion or to a smaller proportion. FIG. 13 shows the hook portions 24 and 26 cross-crossing the loop portion 44 when the elastic bandage is applied to a tapered or curved body part 78. Arrow 45 indicates that the elastic bandage is in a stretched position. Arrow 41 shows the direction in which the bandage is wrapped around the user's body 76 and spiral arrow 43 shows the direction in which the bandage is wrapped around the curved body part 78.

Figure 5:
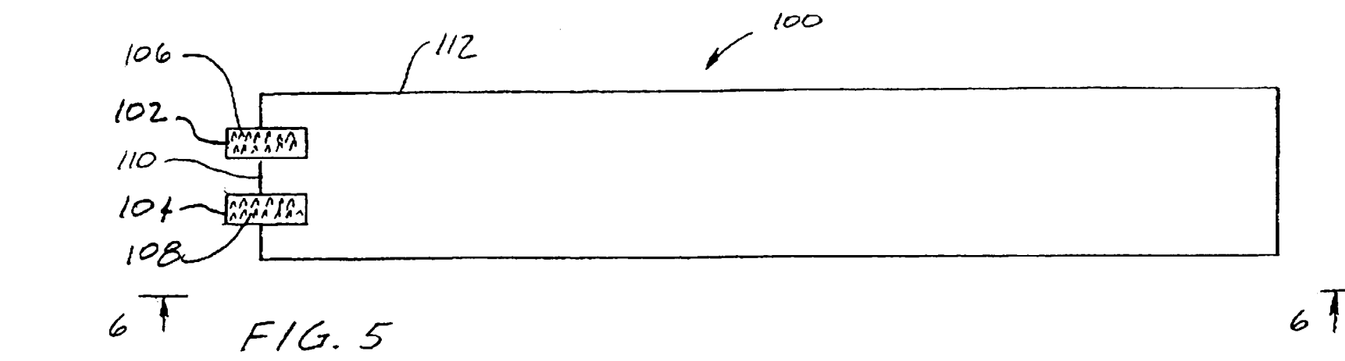
FIG. 5 is a top plan view of an alternative embodiment of the elastic bandage of FIG. 1.
Figure 6:
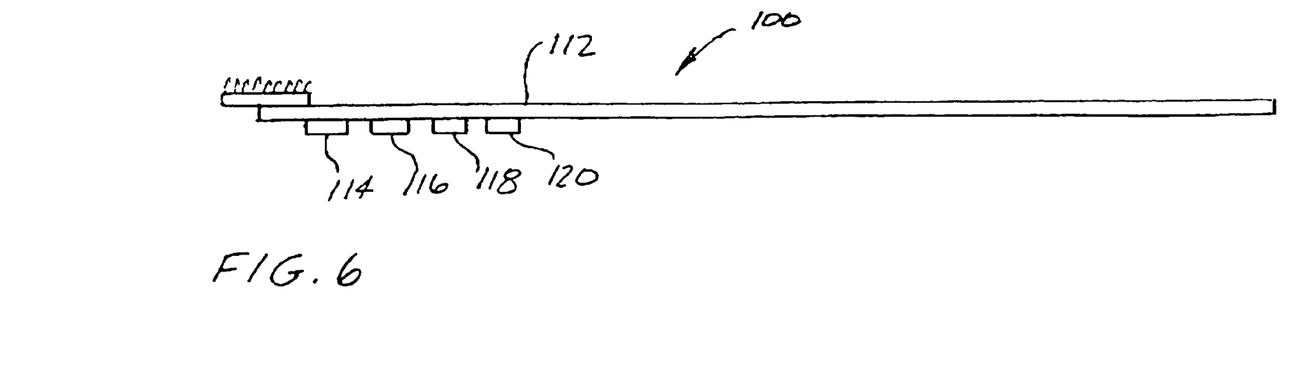
FIG. 6 is a side view of the elastic bandage of FIG. 5 taken along line 6—6 of FIG. 5.

In an alternative embodiment of the invention 100, shown in FIGS. 5 and 6, the edges 102, 104 of the hook portions 106, 108 project beyond the edge 110 of the elastic bandage 112. In the alternative embodiment 100, the loop portions 114, 116, 118, 120 are similar to the loop portions 40, 42, 44, 46 previously described.

Figure 7:
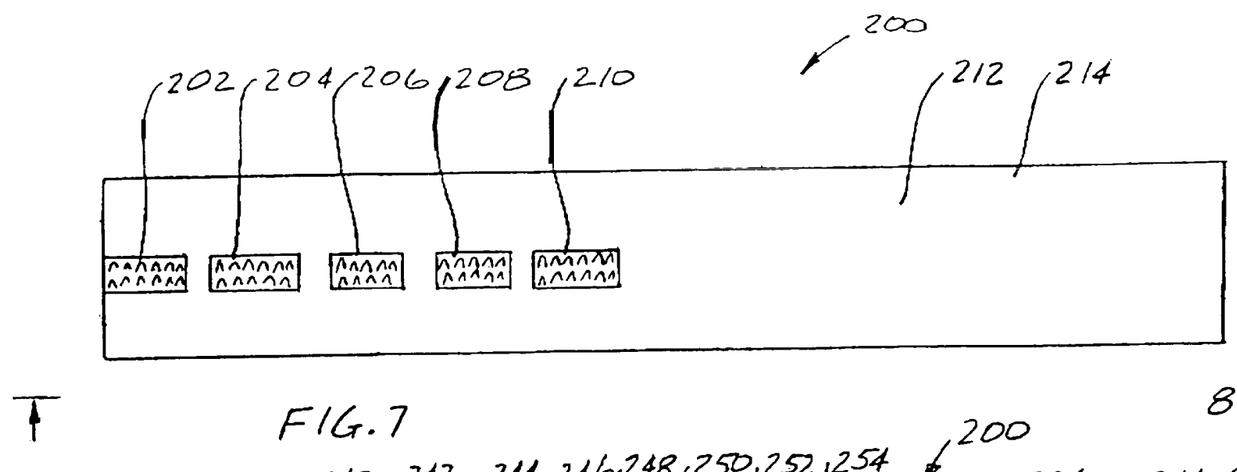
FIG. 7 is a top plan view of another alternative embodiment of the elastic bandage of FIG. 1.
Figure 8:
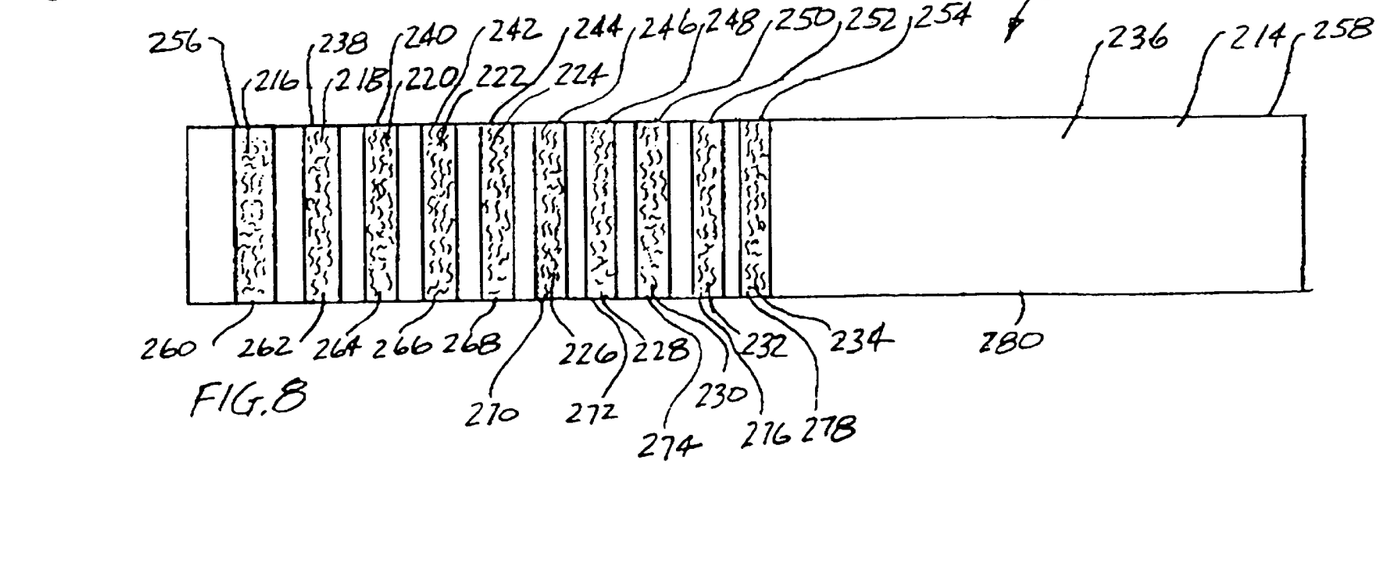
FIG. 8 is a side view of the elastic bandage of FIG. 7 taken along line 8—8 of FIG. 7.

FIGS. 7 and 8 show another alternative embodiment of the invention 200 in which a total of five (5) strips of hook fasteners 202, 204, 206, 208, 210 are oriented in a generally horizontal direction, when viewed as shown in FIG. 7. The hook fasteners 202, 204, 206, 208, 210 are attached to the first side 212 of the elastic bandage 214. As shown in FIG. 8, ten (10) strips of loop fasteners 216, 218, 220, 222, 224, 226, 228, 230, 232, 234 are oriented in a generally vertical direction and the loop fasteners 216, 218, 220, 222, 224, 226, 228, 230, 232, 234 are attached to the second side 236 of the elastic bandage 214. The edges 238, 240, 242, 244, 246, 248, 250, 252, 254, 256 of the loop fasteners 216, 218, 220, 222, 224, 226, 228, 230, 232, 234 are generally in line with the edge 258 of the elastic bandage 214 while the edges 260, 262, 264, 266, 268, 270, 272, 274, 276, 278 are generally in line with the edge 280 of the elastic bandage 214. The hook fasteners 202, 204, 206, 208, 210 are generally centered between the edges 258 and 280 of the elastic bandage 214.

Figure 9:
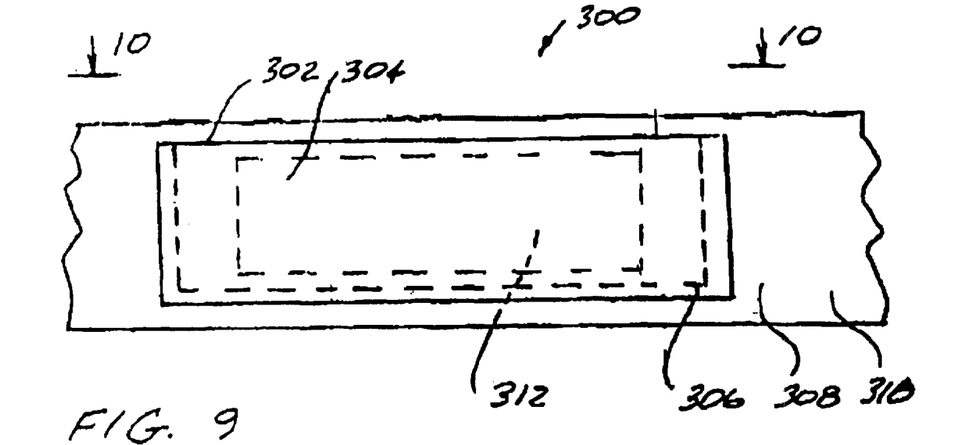
FIG. 9 is a fragmentary top plan view of yet another alternative embodiment of the elastic bandage of FIG. 1.
Figure 10:
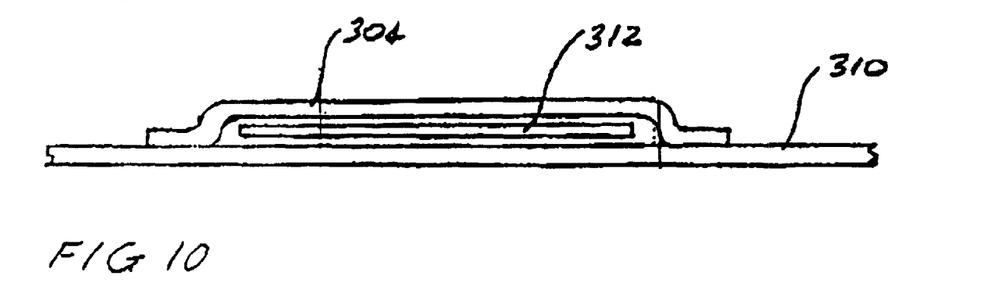
FIG. 10 is a fragmentary side view of the elastic bandage of FIG. 9, taken alone line 10—10 of FIG. 9.

FIGS. 9 and 10 show yet another embodiment of the present invention 300 in which a pocket 302 is formed by a fabric panel 304 which is attached by stitching 306 on an intermediate portion 308 of the elastic bandage 310. A flexible magnet 312 is inserted in the pocket 302, as is shown in FIG. 10, for the purpose of applying magnetic energy to the body. Alternatively a non-magnetic plate which is similar in appearance to the flexible magnet may be inserted into the pocket 302 with the non-magnetic plate having either a curved or a flat shape for the purpose of applying support to the body of a user.

Preferred dimensions and spacing of the hook and loop fastener strips have been found as shown in the following Tables for sides one and two of the elastic bandage. The quantities and proportions are shown for purposes of illustration only and should not be considered as a limitation on the present invention.

| SIDE ONE | |
|---|---|
| Quantity of hook fastener strips | 1 to 5 |
| Width of hook fasteners (inches) | ½ to 6 |
| Length of hook fasteners (inches) | ½ to 6 |
| SIDE TWO | |
| Quantity of loop fasteners | 1 to 10 |
| Width of loop fasteners (inches) | ½ to 10 |
| Length of loop fasteners (inches) | 1 to 8 |
| Spacing between loop fasteners (inches) | ½ to 6 |

Figure 14:
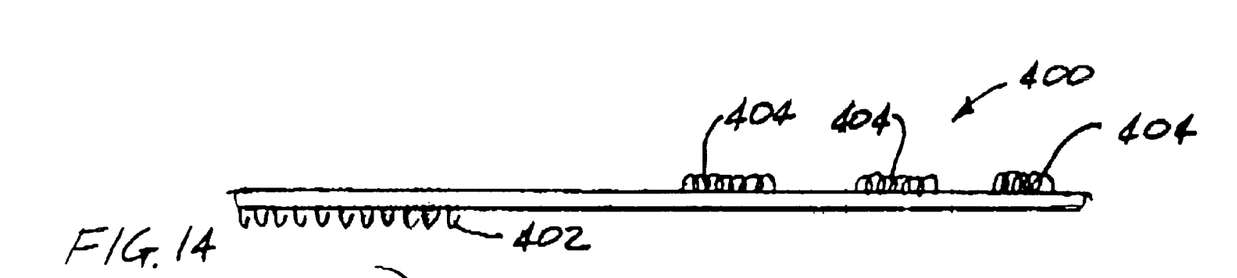
Figure 15:
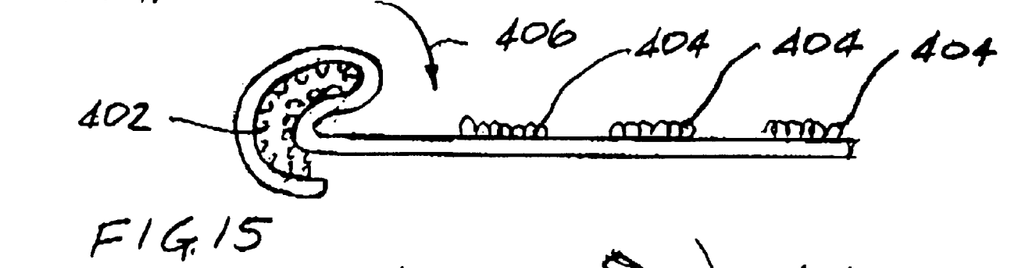
FIG. 15 is a side view showing a preferred method wrapping the bandage of FIG. 14.
Figure 16:
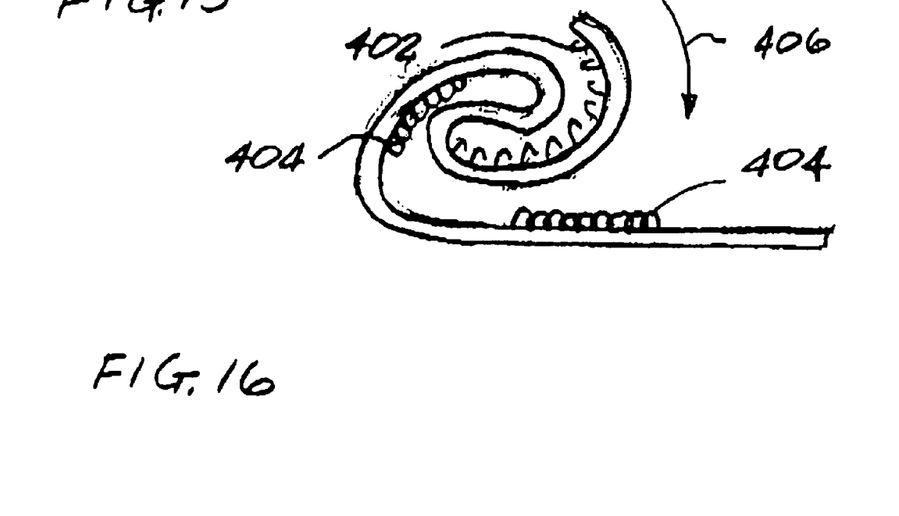
FIG. 16 is a side view similar to FIG. 15, showing the continuation of the process of wrapping the bandage of FIG. 14.

FIGS. 14–16 show a preferred method for wrapping the elastic bandage 400 according to the present invention for storage. The hook portion 402 is folded as shown in FIG. 15 and then the bandage 400 is rolled over the loop portions 404 in the direction shown by the arrow 406 shown in FIGS. 14 and 15. This method maintains the hook portion 402 in an inwardly curled position and prevents the hook portion 402 from curling outwardly when the bandage 400 is wrapped on a user.

Figure 17:
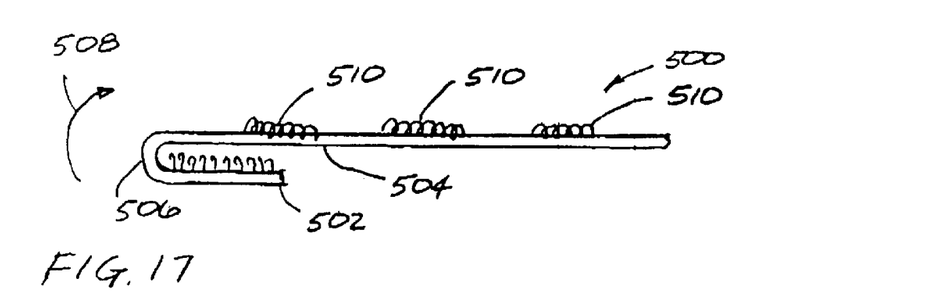
FIG. 17 is a side view similar to FIG. 14, showing an alternative method of wrapping the bandage of FIG. 1.

FIG. 17 shows an alternate method of wrapping the elastic bandage 500 according to the present invention in which the end 502 is folded over onto side 504 and rolling of the bandage 500 begins at the vertex of the fold which is designated by the reference numeral 506. Rolling is performed in the direction shown by the arrow 508 in FIG. 17 with the loop portions 510 always facing the inside or the center of the roll so that when the bandage is unrolled, the loop portions 510 will face the outside.

Figure 18:
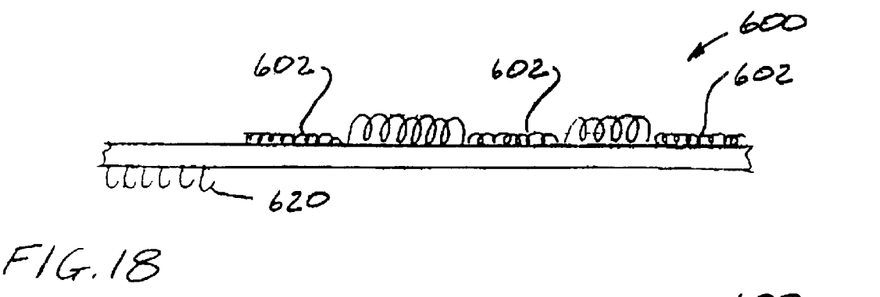
FIG. 18 is a side view showing an alternative embodiment of the invention which incorporates a brush pile surface.
Figure 19:
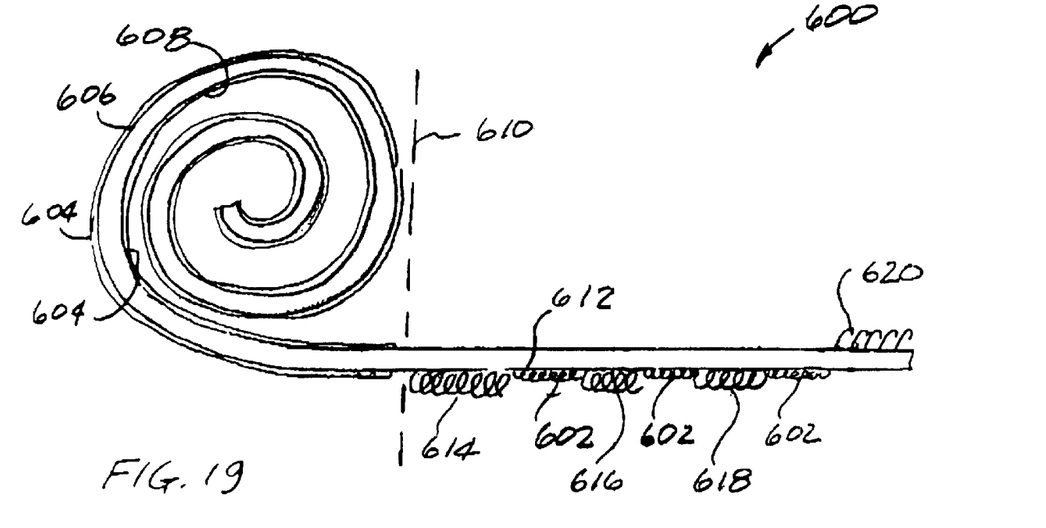
FIG. 19 is a side view showing the embodiment of FIG. 18 partially rolled.

FIGS. 18 and 19 show another alternative embodiment of the invention 600 which incorporates a brush-pile surface 602 and a self-adhering material 604 which is deposited on surface portions 606, 608 of the bandage 600. The self adhering material 604 is also deposited on the portions 606, 608 of the bandage which portions 606, 608 are located to the left of the broken line 610 when viewed as in FIG. 19. FIG. 19 also shows brush-pile surfaces 602 located on the surface 612 of the bandage 600 between the loop portions 614, 616, 618 and between the loop portion 618 and the hook portion 620.

It should be noted that while FIG. 19 shows both an adhesive surface and a brush pile surface, either the adhesive surface or the brush pile surface may be used without the other.

Figure 20:
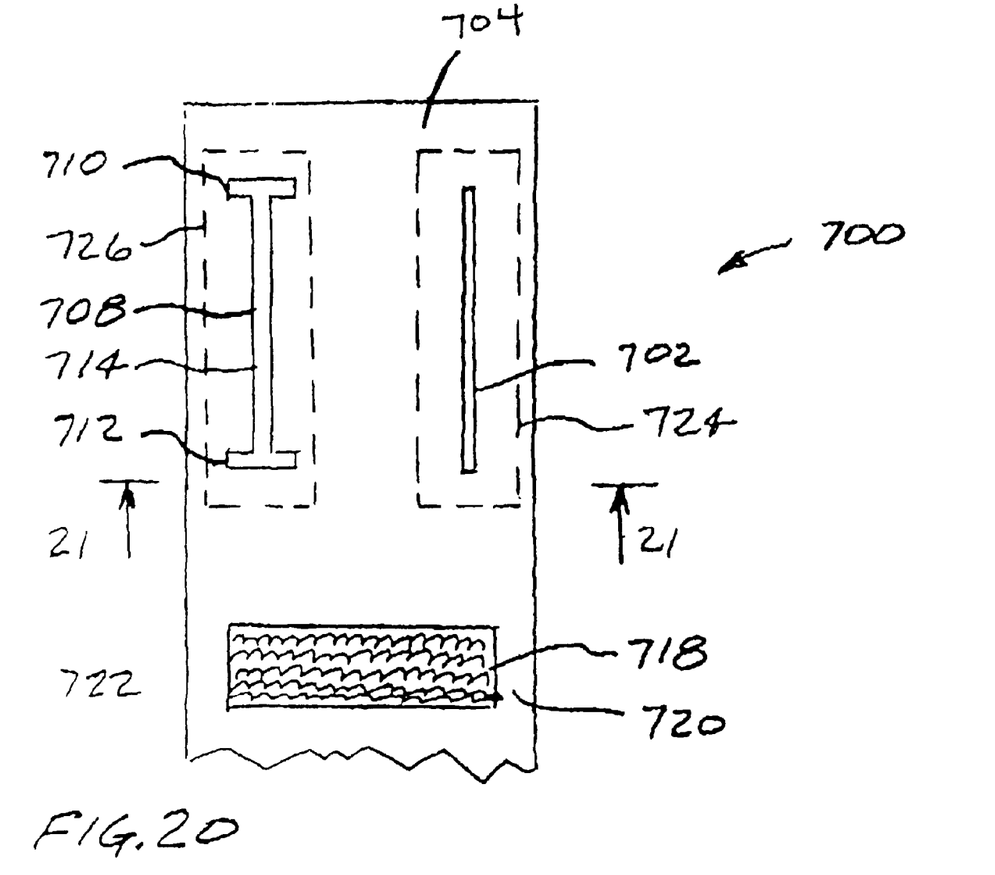
FIG. 20 is a plan view of another alternative embodiment of the invention which incorporates a support on the surface of the bandage opposite the hook strip.
Figure 21:
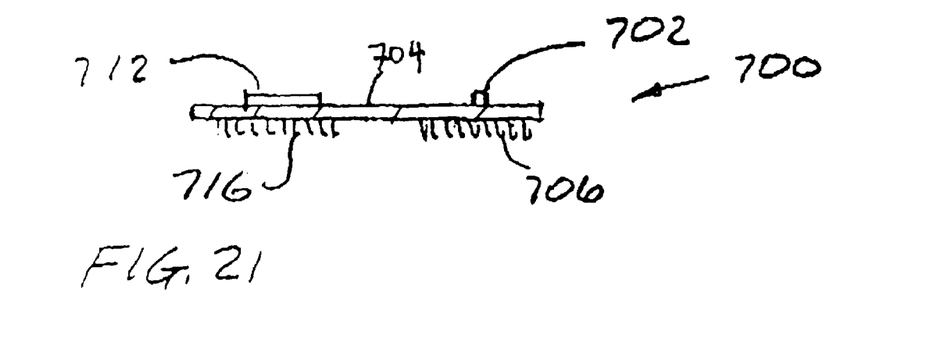
FIG. 21 is a cross-sectional view taken along line 21—21 of FIG. 20.

FIGS. 20 and 21 show another alternative embodiment 700 of the invention in which a support 702 is mounted on the side 704 of the bandage 700 opposite the hook strip 706. The support 702 allows the hook strip 706 to remain at a desired level of inward curl.

Maintaining an inward curl, as is stated above, prevents the hook portions from curling outwardly when the bandage is wrapped on a user. This is beneficial, as it allows the bandage to stay in place longer. The inward curl of the hook portion, additionally, allows for the bandage to fit the contours of ones body more effectively, as the inward curl allows the fastening side to have an enhanced grip of the fastening attachments. Additionally, the inward curl is beneficial as it allows the bandage to fit more securely on a users body as it enhances the grip of the fastening attachments when they are wrapped around a users body.

FIGS. 20 and 21 show an alternative support 708 which incorporates end bars 710, 712. The end bars 710, 712 are generally perpendicular to the central portion 714 of the support 708 and provide additional control over the curl of the hook strip 716.

FIG. 20 also shows an alternative embodiment of the loop portion 718 which is somewhat shorter in length than the width of the bandage 700. The loop portion 718 is centered on the bandage 700 leaving the two portions 720, 722 of the bandage 700 free. FIG. 20 shows the hook portions 716, 706 attached to the bandage 700 by stitching 724, 726.

Figure 22:
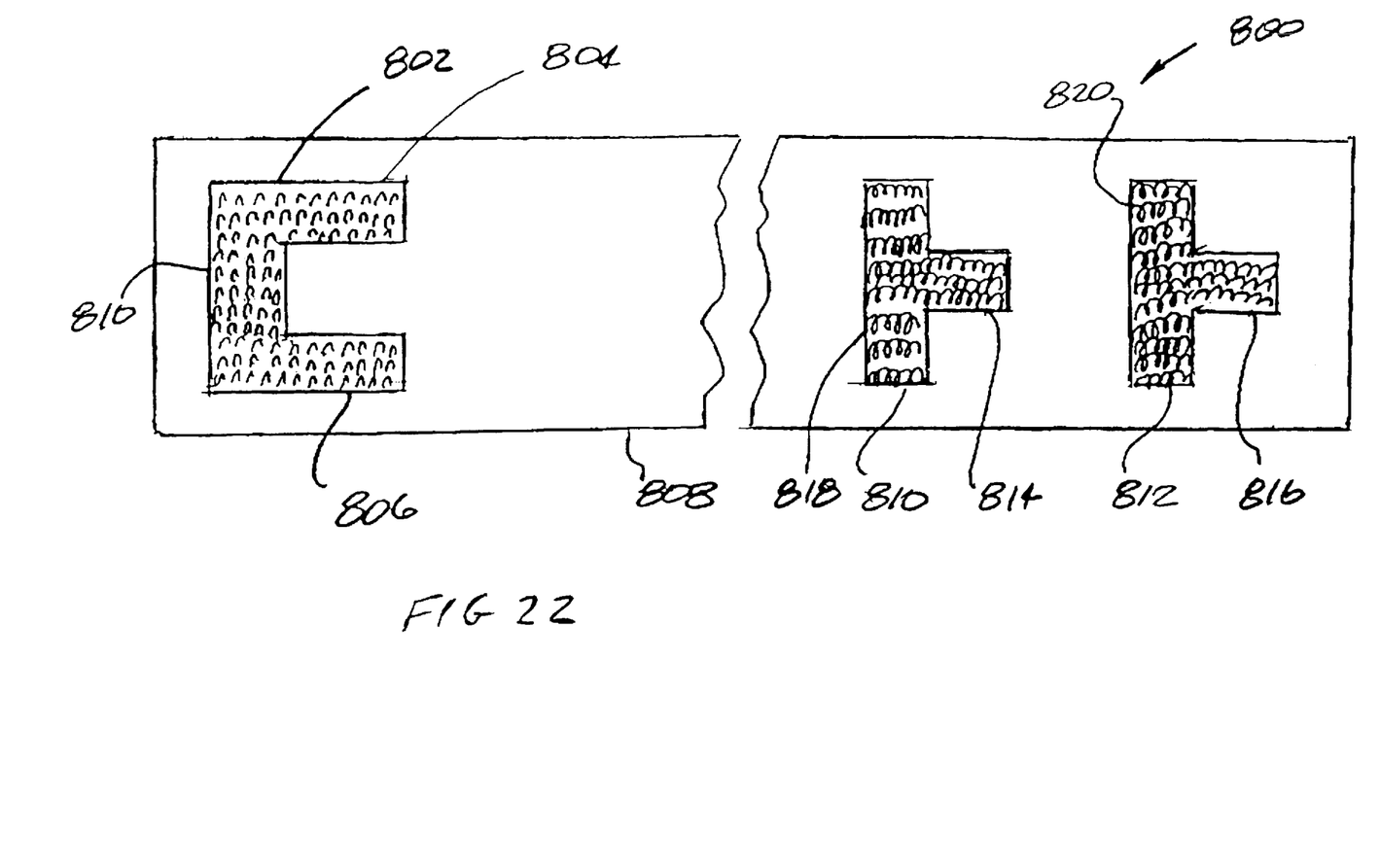
FIG. 22 is a plan view of another alternative embodiment of the invention in which the hook and loop portions have segments which are aligned with any angle relative to the length dimension of the bandage.

FIG. 22 shows another alternative embodiment of the invention 800 in which a hook portion 802 has segments 804, 806 which may be aligned with any angle relative to the length dimension or edge 808 of the bandage 800 and a segment 810 which is aligned with the width dimension of the bandage 800. The segments 804, 806 are shown by way of example only as being in general alignment with the length dimension of the bandage 800.

In the embodiment of the invention 800 shown in FIG. 22, the loop portions 810, 812 have segments 814, 816 which may be aligned with any angle relative to the length dimension of the bandage 800 and segments 818, 820 are aligned with the width dimension of the bandage 800. The segments 814, 816 are shown by way of example only to be aligned with the length dimension of the bandage 800.

FIGS. 23–26 show another alternative embodiment 900 of the invention in which the hook portion 902 and/or the loop portion 904 have elasticity.

Figure 23:
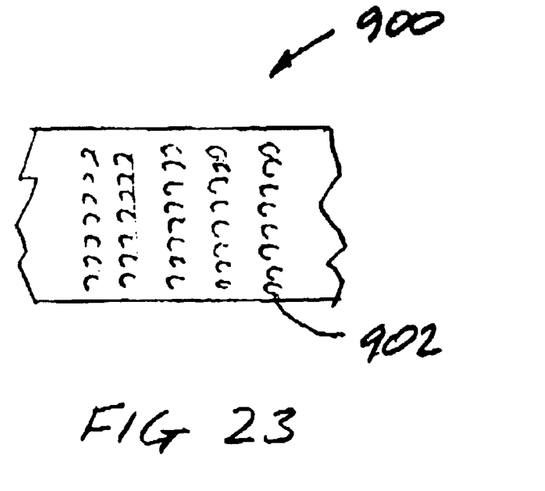
FIGS. 23–26 are plan views of another alternative embodiment of the invention in which the hook and the loop portions each incorporate elastic characteristics.
Figure 24:
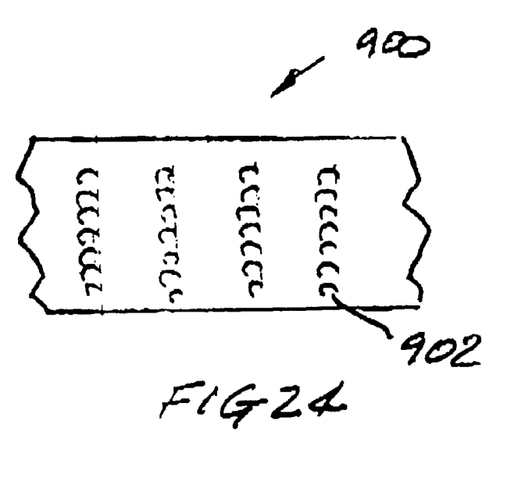
Figure 25:
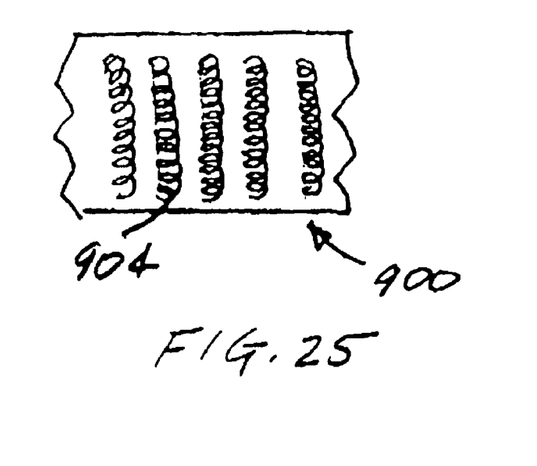
Figure 26:
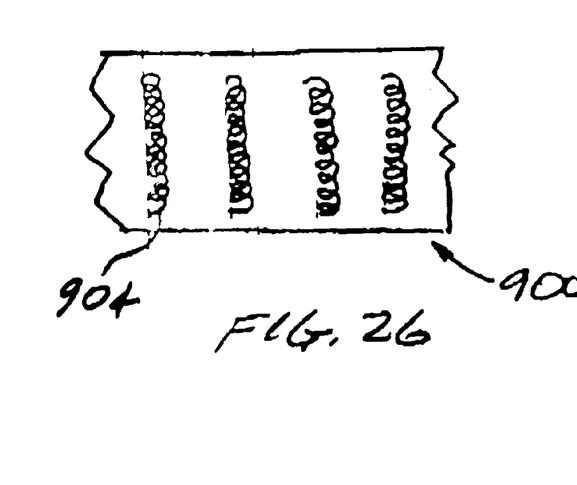

FIGS. 23 and 25 show hook and loop portions 902, 904 respectively in the unstretched condition. FIGS. 24 and 26 show the hook 902 and loop 904 portions in the stretched condition.

Figure 27:
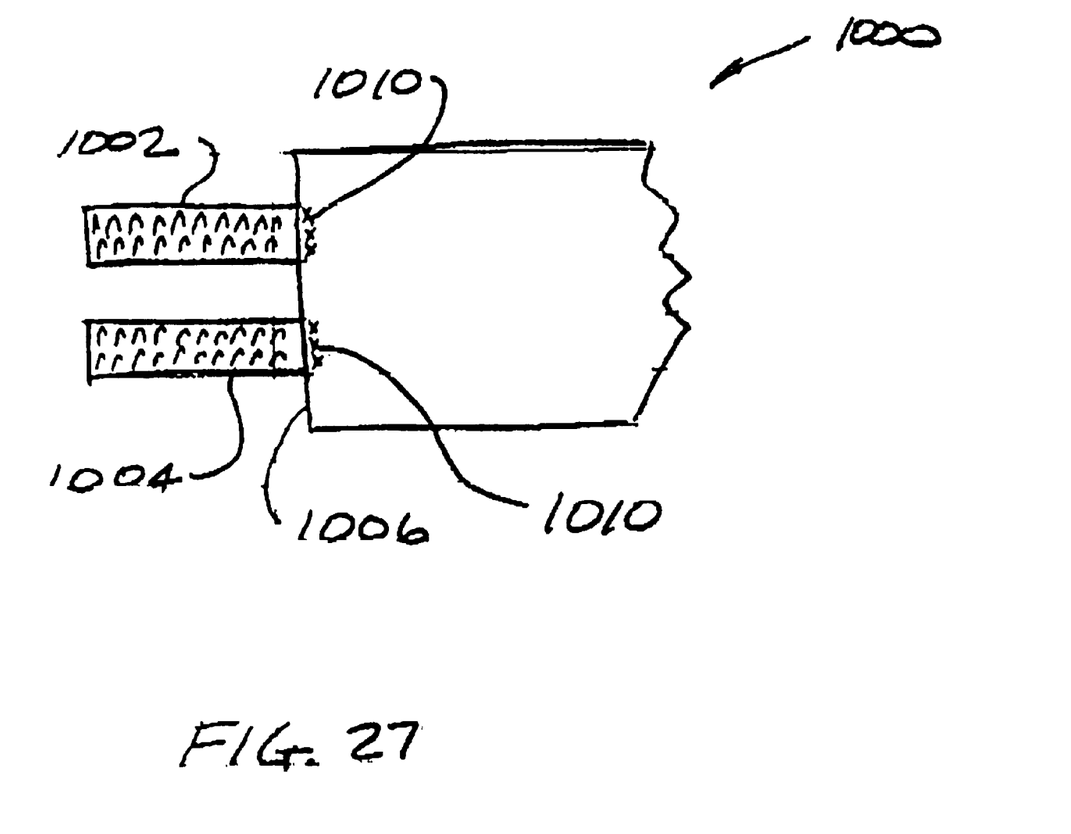
FIG. 27 is a plan view of another alternative embodiment of the present invention in which a hook portion of a hook and loop fastener is attached to the end of the elastic bandage.

FIG. 27 shows another alternative embodiment of the invention 1000 in which a pair of hook portions 1002 and 1004 are attached to the end 1006 of an elastic bandage 1008 by stitching 1010.

Figures 28, 29, 30, 31:
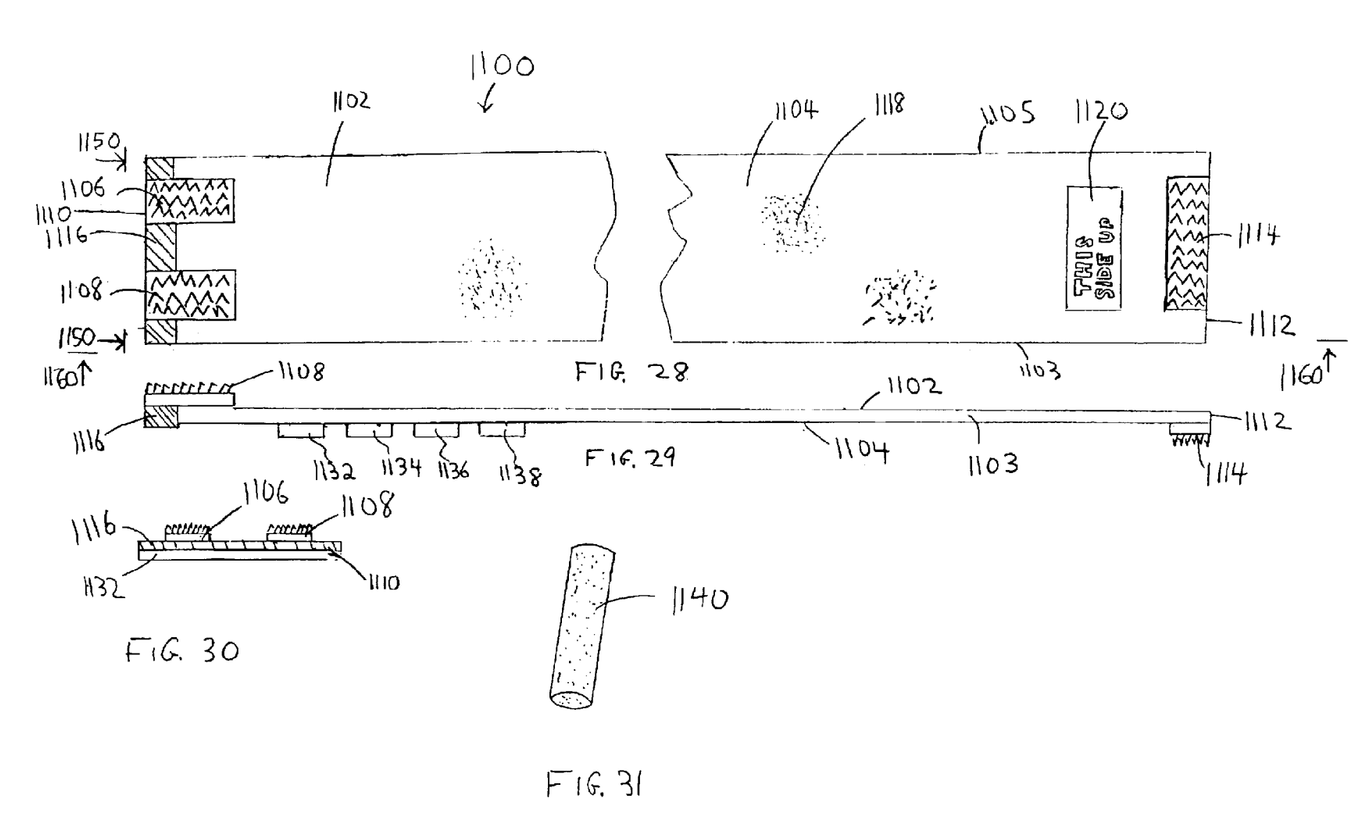
FIG. 28 is a top view of a further embodiment of the invention which incorporates a reinforcement, an initial engagement strip, hypoallergenic fibers and an indicum.
FIG. 29 is a side view of the elastic bandage taken along line 1160—1160 of FIG. 28.
FIG. 30 is an end view of the elastic bandage taken along line 1150—1150 of FIG. 28.
FIG. 31 is a segment of a hypoallergenic elastic fiber as is used in the elastic bandage of FIG. 28.

FIG. 28 shows another embodiment of the invention 1100, which is comprised of a first surface 1102, a second surface 1104, a first end 1110, a second end 1112, and longer edges 1103 and 1105. The first end 1110 of the elastic bandage 1100 has a pair of hook portions 1106, 1108 affixed to it and additionally has reinforcement 1116 attached to it to prevent unwanted unraveling of the elastic bandage 1100. On the second surface 1104 of the bandage 1100 disposed transversely and proximate to the second end 1112 of the bandage 1100 there is a strip of friction adding material 1114 which in this illustration is presented as a strip of hook fastener. This strip 1114 will come into contact with the first surface 1102, when the bandage 1100 is being wrapped, and by increasing the friction between the two surfaces 1104 and 1102 will aid the user in making his initial wrap of the bandage 1100. An indicium 1120 is printed onto bandage 1100 which in this illustration reads "This Side Up" to indicate to a user the proper placement of the bandage 1100. Furthermore, the elastic bandage 1100 is itself comprised of elastic fibers 1118 that are hypoallergenic.

It should be noted that although FIG. 28 shows a bandage comprised of friction adding material, reinforcing material, hypoallergenic fibers and an indicium, any of these may be used without the others.

As is shown in FIG. 29, a plurality of loop portions 1132, 1134, 1136, 1138 are disposed on the second surface 1104 of the elastic bandage 1100. The reinforcement 1116 is covering the sides 1103 and 1105 of the bandage 1100. In FIG. 30 the reinforcement is seen covering the end portion 1110 of the bandage 1100. The reinforcement 1116 may be made of any substance or material and may have elastic or inelastic properties.

In FIG. 31 there is shown a section of elastic fiber 1140 used in bandage 1100 which is hypoallergenic and will therefore protect a user from an allergic reaction to bandage 1100.

Figure 32:
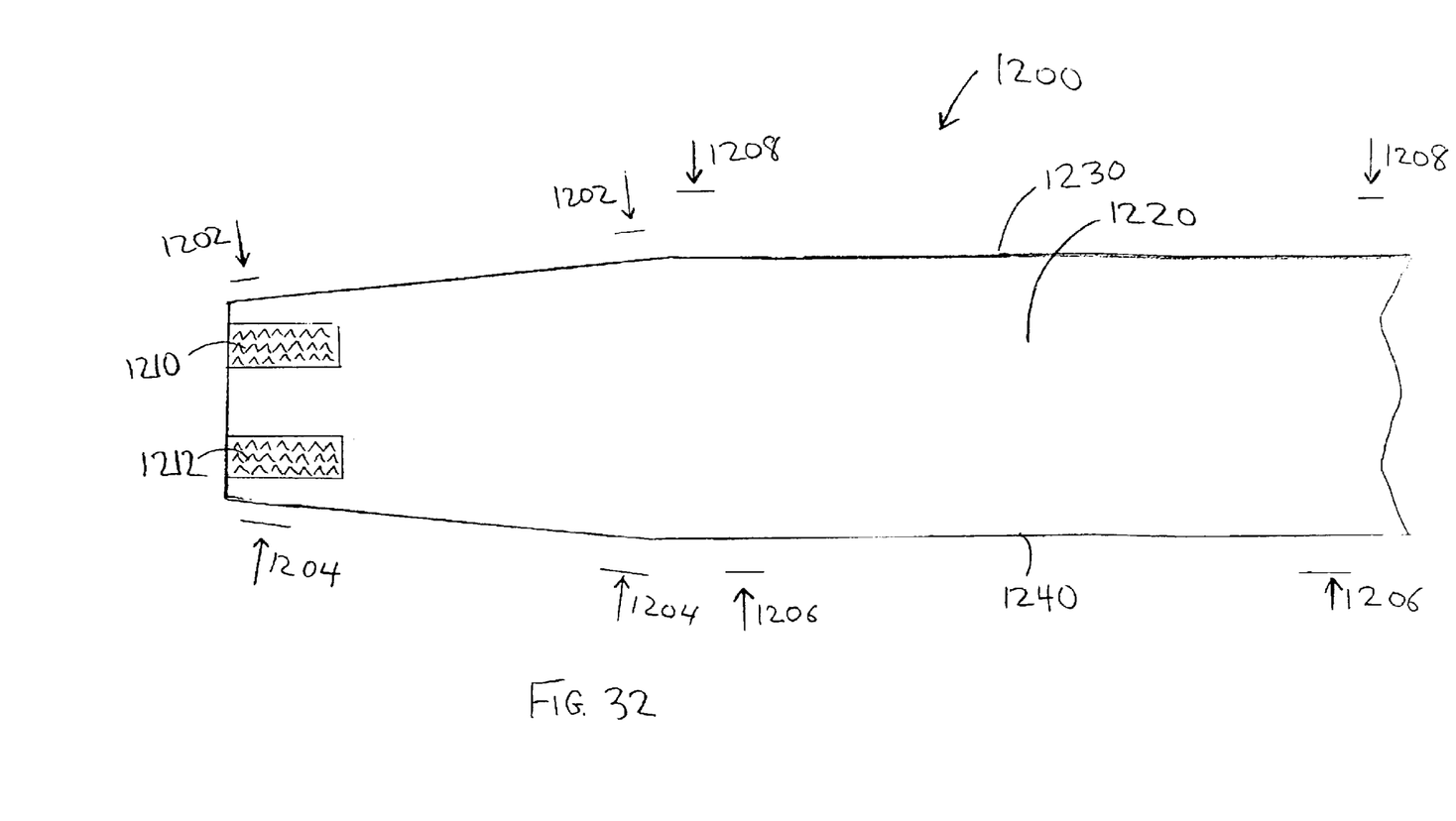
FIG. 32 is an alternative embodiment of the invention disposed on an elastic bandage which is itself tapered.

The present invention can also be applied to a bandage such as FIG. 32. Elastic bandage 1200 is of tapered proportions such that the longitudinal edges 1230 along line 1208—1208 and the longitudinal edge 1240 along line 1206—1206 are parallel with respect to one another and the longitudinal edges 1230 and 1240 become tapered along lines 1202—1202 and 1204—1204. Longitudinally disposed hook strips 1210 and 1212 are affixed to the first surface 1220 of bandage 1200.

The present invention contemplates the combination of an elastic bandage with hook and loop fasteners and one or more of the following:

at least one portion of a brushpile surface disposed on the same side of the elastic bandage as the loop portion of the hook and loop fastener;

at least one portion of an adhesive layer disposed on at least one side of the elastic bandage;

at least one support member disposed on the elastic bandage and disposed opposite at least one fastener of the hook and loop fastener;

at least one fastener of the hook and loop fastener having at least one elongated segment forming an angle with the length dimension of the elastic bandage;

at least one fastener of the hook and loop fastener having elasticity; a pocket panel attached to the elastic bandage;

at least one reinforcing material disposed on at least one edge or end of the bandage;

at least one indicium disposed on at least one side of the bandage;

at least one friction adding material disposed on at least one side of the elastic; and an elastic bandage composed of hypoallergenic fibers.

The foregoing specific embodiments of the present invention as set forth in the specification herein are for illustrative purposes only. Various deviations and modifications can be made within the spirit and scope of this invention, without departing from the main theme thereof.

What is claimed is:

1. A bandage apparatus, comprising:

an elongated elastic bandage with a first surface, a second surface, a first end, and a second end;

a plurality of longitudinal hook and loop fastener portions, wherein
  said longitudinal hook and loop fastener portions are attached to said first surface of said bandage, wherein
    said longitudinal hook and loop fastener portions are positioned only adjacent said first end of said bandage;
    said longitudinal hook and loop fastener portions are elongated along a longitudinal direction of said bandage;
    said longitudinal hook and loop fastener portions are spaced apart from each other; and
a plurality of transverse hook and loop fastener portions, wherein
  said transverse hook and loop fastener portions are attached to said second surface of said bandage;
  said transverse hook and loop fastener portions are attached only adjacent said first end of said bandage;
  said transverse hook and loop fastener portions are elongated along a transverse direction of said bandage;
  said transverse hook and loop fastener portions are spaced apart from each other;
  said longitudinal hook and loop fastener portions are arranged at said first end of said bandage, wherein at least one of said longitudinal hook and loop fastener portions and at least one of said transverse hook and loop fastener portions are generally directly opposite each other in overlaying criss-crossed configuration on either surface of said bandage;
  said second end of said bandage is devoid of any fasteners;
  and a plurality of elongated support members disposed on said second surface of said bandage directly opposite and overlaying said longitudinal hook and loop fastener portions to maintain said longitudinal hook and loop fastener portions at a predetermined level of inward curl of said longitudinal hook and loop fastener portions.

2. The bandage apparatus of claim 1, wherein said longitudinal hook and loop fastener portions and said transverse hook and loop fastener portions are elastic.

3. The bandage apparatus of claim 1, wherein said support member is comprised of an I-beam shaped member with perpendicular end bars at opposite ends of a central portion.

* * * * *